United States Patent
Ying et al.

(10) Patent No.: US 10,386,435 B2
(45) Date of Patent: Aug. 20, 2019

(54) METHODS AND SYSTEMS FOR FAST AUTO-CALIBRATED RECONSTRUCTION WITH RANDOM PROJECTION IN PARALLEL MRI

(71) Applicant: The Research Foundation for the State University of New York, Amherst, NY (US)

(72) Inventors: Lei Leslie Ying, East Amherst, NY (US); Jingyuan Lv, Buffalo, NY (US)

(73) Assignee: The Research Foundation for The State University of New York, Buffalo, NY (US)

( * ) Notice: Subject to any disclaimer, the term of this patent is extended or adjusted under 35 U.S.C. 154(b) by 680 days.

(21) Appl. No.: 14/535,143

(22) Filed: Nov. 6, 2014

(65) Prior Publication Data

US 2015/0127291 A1    May 7, 2015

Related U.S. Application Data

(60) Provisional application No. 61/900,574, filed on Nov. 6, 2013.

(51) Int. Cl.
  *G01R 33/58*   (2006.01)
  *G01R 33/561*  (2006.01)
  *A61B 5/055*   (2006.01)

(52) U.S. Cl.
  CPC ......... *G01R 33/5611* (2013.01); *A61B 5/055* (2013.01)

(58) Field of Classification Search
  None
  See application file for complete search history.

(56) References Cited

U.S. PATENT DOCUMENTS 8,170,311 B2   5/2012 Ying
2006/0273792 A1* 12/2006 Kholmovski ...... G01R 33/5611
                                                   324/309

(Continued)

FOREIGN PATENT DOCUMENTS

CN        103679654       3/2014

OTHER PUBLICATIONS

Chunlei Liu, Auto-Calibrated Parallel Imaging Reconstruction for Arbitrary Trajectories Using k-Space Sparse Matrices (kSPA), IEEE Transactions on Medical Imaging, vol. 29, No. 3, Mar. 2010, pp. 950-959.*

(Continued)

*Primary Examiner* — Tung S Lau
(74) *Attorney, Agent, or Firm* — Hodgson Russ LLP

(57) ABSTRACT

Methods and systems for fast auto-calibrated reconstruction with random projection in parallel MRI are disclosed. In one embodiment, calibration and reconstruction are accelerated by reducing the number of k-space data channels before calibration. During calibration, a random projection is performed in order to reduce the dimensionality of the calibration equation. The reduced-dimensionality equation is used to obtain the reconstruction coefficients, which are then used to synthesize reconstructed k-space data. The received and reconstructed k-space data together construct a parallel MRI image. Systems for fast GRAPPA reconstruction are disclosed comprising a processor configured, for example, through software, to collect k-space data, reduce the number of data channels, perform the random projection, solve a reduced calibration equation, and synthesize the k-space data to construct a final parallel MRI image.

11 Claims, 13 Drawing Sheets

(56) References Cited

U.S. PATENT DOCUMENTS

| | | |
|---|---|---|
| 2011/0243381 A1 | 10/2011 | Tsagkatakis et al. |
| 2013/0028516 A1 | 1/2013 | Warfield et al. |
| 2013/0278256 A1 | 10/2013 | Ahmad et al. |
| 2013/0336588 A1 | 12/2013 | Rane et al. |

OTHER PUBLICATIONS

Achlioptas, Database-friendly random projections: Johnson-Lindenstrauss with binary coins, Journal of Computer and System Sciences 66 (2003), pp. 671-687. Jan. 1, 2003.

Huang et al., A software channel compression technique for faster reconstruction with many channels, Magnetic Resonance Imaging 26 (2008), pp. 133-141. Jan. 1, 2008.

Pawar et al., Accelerating k-t sparse using k-space aliasing for dynamic MRI imaging, 2013 35th Annual International Conference of the IEEE Engineering in Medicine and Biology Society (EMBC), pp. 2619-2623. Jan. 1, 2013.

Lee et al., Rapid time-resolved magnetic resonance angiography via a multiecho radial trajectory and GraDeS reconstruction, Apr. 3, 2012, Magn. Reson. Med. 69(2), pp. 346-359. Apr. 3, 2012.

\* cited by examiner

METHODS AND SYSTEMS FOR FAST AUTO-CALIBRATED RECONSTRUCTION WITH RANDOM PROJECTION IN PARALLEL MRI

CROSS-REFERENCE TO RELATED APPLICATIONS

This application claims priority to U.S. Provisional Application No. 61/900,574, filed on Nov. 6, 2013, now pending, the disclosure of which is incorporated herein by reference.

STATEMENT REGARDING FEDERALLY SPONSORED RESEARCH

This invention was made with government support under grant no. CBET1265612 awarded by the National Science Foundation. The government has certain rights in the invention.

FIELD OF THE INVENTION

The invention relates to parallel magnetic resonance imaging (pMRI) reconstruction methods and systems. Specifically, methods and systems for fast auto-calibrated reconstruction techniques such as generalized auto-calibrating partially parallel acquisition (GRAPPA) with random projection in pMRI.

BACKGROUND OF THE INVENTION

In magnetic resonance imaging (MRI), a sample (e.g., a human subject) is placed in a powerful magnetic field. In the magnetic field, the hydrogen protons in the sample will align with the magnetic field in one direction or the other. The MRI machine applies a radio pulse configured specifically to affect hydrogen. The radio pulse causes the protons in a region of interest to absorb energy and spin in a different direction and at a particular frequency. At same time, or approximately the same time, gradient fields are turned on and off very rapidly in a specific manner, which alter the main magnetic field on a local level. When the radio pulse is turned off, the hydrogen protons begin to return to their natural alignment within the magnetic field and release their excess stored energy in form of radio waves. The radio waves are then detected by one or more receiver coils. The data that is collected by the receiver coils is in the form of spatial frequencies, in what is called "k-space" of the image. Frequency data in k-space can be mathematically converted to a recognizable image in the so-called image domain using a number of procedures, including for example a Fourier transform. Reconstructions of images of the sample (e.g., a human subject's brain or heart) take into account information about the orientations of applied magnetic fields and the orientations of the receiver coils.

Despite numerous advances in the field, one drawback of MRI has been the slow rate at which data is collected, such that long scanning times may be required. Subjects may be unable to remain sufficiently still for the amount of time required to obtain an image, and blurring artifacts from motion can arise which degrade the quality of the MR images.

Parallel MRI (pMRI) is a method that has been developed to address this problem. pMRI uses multiple detector coils and has each coil collect less data, thus allowing for faster scanning times. Parallel MRI uses an array of RF receiver surface coils to simultaneously (or near-simultaneously) acquire multiple sets of under-sampled k-space data. While this technique allows faster scanning of the sample, the under-sampled data that is collected has a reduced signal-to-noise ratio (SNR). The k-space data collected using pMRI is a complex combination of the actual sample data modified by the relative sensitivities of each receiver coil.

Accordingly, parallel imaging using phased array coils has been used clinically to accelerate MR data acquisition speed. Higher data acquisition rates can be achievable by using coils with more data channels. Massive array coils with a large number of data channels have been studied and developed. As a result, the data acquisition times can be reduced at the expense of reconstruction time following data acquisition. As such massive array coils become commercially available, the greatly increased computational time has become a concern to reconstruct MR images from reduced acquisitions with multiple receivers.

A number of techniques, operating in either k-space or the image domain, have been proposed for reconstructing a complete MR image from under-sampled data. Among the commercial reconstruction methods, GRAPPA is used as one of the auto-calibrated reconstruction techniques. GRAPPA reconstructs missing k-space data for each channel (known as the target channel) by a linear combination of some acquired data from all channels (source channels), where the coefficients for the linear combination are estimated using additionally acquired auto-calibration signal (ACS) lines. In conventional GRAPPA, both the number of source channels and the number of target channels are equal to the number of physical channels of the coil. Because of such channel-by-channel calculation, the computation time of GRAPPA increases almost quadratically with the number of channels. Therefore, GRAPPA causes long reconstruction times when massive array coils are used. Other auto-calibrated reconstruction methods, like SPIRiT, suffer from the same disadvantages. This leads to difficulties in real-time and high-throughput imaging.

Some attempts have been made to address this issue by reducing the effective number of channels using hardware-based or software-based approaches. In the hardware-based approach, an inline hardware RF signal combiner is used after pre-amplification and before the receiver system. This effectively constructs an eigencoil array based on the noise covariance of the receiver array. Optimal SNR and similar reconstruction qualities can be achieved using such a channel reduction. However, the required hardware can be cumbersome and expensive.

In contrast, software-based channel reduction methods are more flexible. Software coil compression processes generate a new set of fewer virtual channels that can be expressed as linear combinations of the physical channels. These methods aim at reducing the effective number of channels used for reconstruction by combining the physically acquired data from a large number of channels before image reconstruction. For example, principal component analysis (PCA) has been used to find the correlation among physical channels and reduce the number of channels to fewer effective ones by linearly combining the data from physical channels. These fewer combined channels are used for reconstruction, which leads to reduced reconstruction time. A major limitation of PCA is its computation complexity. Performing a PCA requires an order of $N^3$ multiplications, with N being the original dimension, which becomes prohibitive when dealing with a large data set as found in modern pMRI systems.

BRIEF SUMMARY OF THE INVENTION

Embodiments of the present disclosure can accelerate pMRI reconstruction in the k-space domain. In one embodiment, the invention is a method of pMRI comprising (a) acquiring pMRI signals simultaneously through a plurality of receiving coils, where in each coil has a localized sensitivity with respect to an imaged volume; (b) using auto calibration pMRI signals to fast estimate the fitting coefficients for each coil with random projection.

In another embodiment, the invention is a method of pMRI comprising integration of channel reduction and random projection to further accelerate reconstruction (CR-RP-GRAPPA). The channel reduction is performed before calibration and random projection is performed during the calibration step.

One embodiment of the present disclosure is as a method for constructing a parallel magnetic resonance image. The method comprises the step of receiving, at a processor, a plurality of k-space signals. Each k-space signal may correspond to a channel of a receiver coil. Each k-space signal may comprise a combination of sample data corresponding to the parallel magnetic resonance image and sensitivity information of a channel.

The method further comprises the step of selecting, using the processor, a subset of the plurality of k-space signals. The plurality of k-space signals may be selected using principal component analysis, or another suitable algorithm.

The method further comprises the step of receiving, at the processor, a plurality of auto-calibration signals.

The method further comprises the step of selecting, using the processor, a subset of the plurality of auto-calibration signals. In one embodiment, the step of selecting a subset of the plurality of k-space signals comprises:
  a) defining, using the processor, a set of N vectors. N may equal the total number of channels associated with the plurality of k-space signals;
  b) calculating, using the processor, a mean corresponding to each vector in the set of N vectors;
  c) subtracting from each vector in the set of N vectors, using the processor, the calculated mean associated from its corresponding vector;
  d) calculating, using the processor, a covariance matrix;
  e) calculating, using the processor, a plurality of eigenvectors of the covariance matrix;
  f) creating, using the processor, a compression matrix based on the plurality of eigenvectors; and
  g) selecting, using the processor, a subset of the plurality of k-space signals by multiplying the plurality of k-space signals by the compression matrix.

The method further comprises the step of determining, using the processor, a first calibration equation. The first calibration equation may be associated with the selected auto-calibration signals and the selected k-space signals.

The method further comprises the step of reducing, using the processor, the first calibration equation. The reduced calibration equation has a lesser dimensionality than the first calibration equation. The first calibration equation may be reduced by randomly selecting a subset of the first calibration equation. The first calibration equation may also be reduced by multiplying the first calibration equation with a random projection matrix. For example, the random projection matrix may comprise elements from the following distribution:

$$R_{(i,j)} = \sqrt{3} \begin{cases} 1 & p = 1/6 \\ 0 & p = 2/3 \\ -1 & p = 1/6 \end{cases}$$

The method further comprises the step of determining, using the processor, a plurality of reconstruction coefficients. The plurality of reconstruction coefficients may be based on the reduced calibration equation. Each coefficient may correspond to a channel of the receiver coil. The plurality of reconstruction coefficients may be determined using a least-squares method. In another embodiment, the plurality of reconstruction coefficients may be determined using a cost function minimization algorithm. For example, the cost function minimization algorithm may calculate the plurality of reconstruction coefficients under a specified constraint such as the l1-norm or l2-norm. The plurality of reconstruction coefficients may also be based on a sensitivity of the receiver coil.

The method further comprises the step of synthesizing, using the processor, reconstructed k-space data. The reconstructed k-space data may be based on the plurality of reconstruction coefficients and received k-space signals.

The method further comprises the step of constructing, using the processor, a parallel magnetic resonance image based on the reconstructed k-space data.

One embodiment of the present disclosure is as a system for constructing a parallel magnetic resonance image. The system may comprise a parallel magnetic resonance imaging device. The pMRI device may have a plurality of receiver coils. Each receiver coil may have a plurality of channels.

The system may further comprise an image reconstruction device. The image reconstruction device may be in electronic communication with the parallel magnetic resonance imaging device.

The image reconstruction device may comprise an electronic storage device. The electronic storage device may be configured to contain data corresponding to a parallel magnetic resonance image.

The image reconstruction device may also comprise a processor. The processor may be in electronic communication with the electronic storage device and the parallel magnetic resonance imaging device.

The processor may be configured to receive a plurality of k-space signals from the parallel magnetic imaging device. Each k-space signal may correspond to a channel of a receiver coil. Each k-space signal may comprise a combination of sample data corresponding to the parallel magnetic resonance image and sensitivity information of a channel.

The processor may also be configured to select a subset of the plurality of k-space signals. The processor may be configured to select a subset of the plurality of k-space signals using principal component analysis.

The processor may also be configured to receive a plurality of auto-calibration signals from the parallel magnetic imaging device or electronic storage device.

The processor may also be configured to select a subset of the plurality of auto-calibration signals.

The processor may also be configured to determine a first calibration equation associated with the selected auto-calibration signals and the selected k-space signals.

The processor may also be configured to reduce the first calibration equation to a reduced calibration equation having a lesser dimensionality than the first calibration equation. The processor may be configured to reduce the first calibration equation by randomly selecting a subset of the first calibration equation. The processor may also be configured to reduce the first calibration equation by multiplying the first calibration equation with a random projection matrix. The random projection matrix may comprise elements from the following distribution:

$$R_{(i,j)} = \sqrt{3} \begin{cases} 1 & p = 1/6 \\ 0 & p = 2/3 \\ -1 & p = 1/6 \end{cases}$$

The processor may also be configured to determine a plurality of reconstruction coefficients based on the reduced calibration equation. Each reconstruction coefficient may correspond to a channel of the receiver coil. The processor may be configured to determine the plurality of reconstruction coefficients based on a sensitivity of the receiver coil. The processor may also be configured to determine the plurality of reconstruction coefficients using a cost function minimization algorithm. The cost function minimization algorithm may cause the processor to calculate the plurality of reconstruction coefficients under a specified constraint.

The processor may also be configured to synthesize reconstructed k-space data based on the plurality of reconstruction coefficients and received k-space signals.

The processor may also be configured to construct a parallel magnetic resonance image based on the reconstructed k-space data.

DESCRIPTION OF THE DRAWINGS

For a fuller understanding of the nature and objects of the disclosure, reference should be made to the following detailed description taken in conjunction with the accompanying drawings, in which.

DETAILED DESCRIPTION OF THE INVENTION

Figure 14:
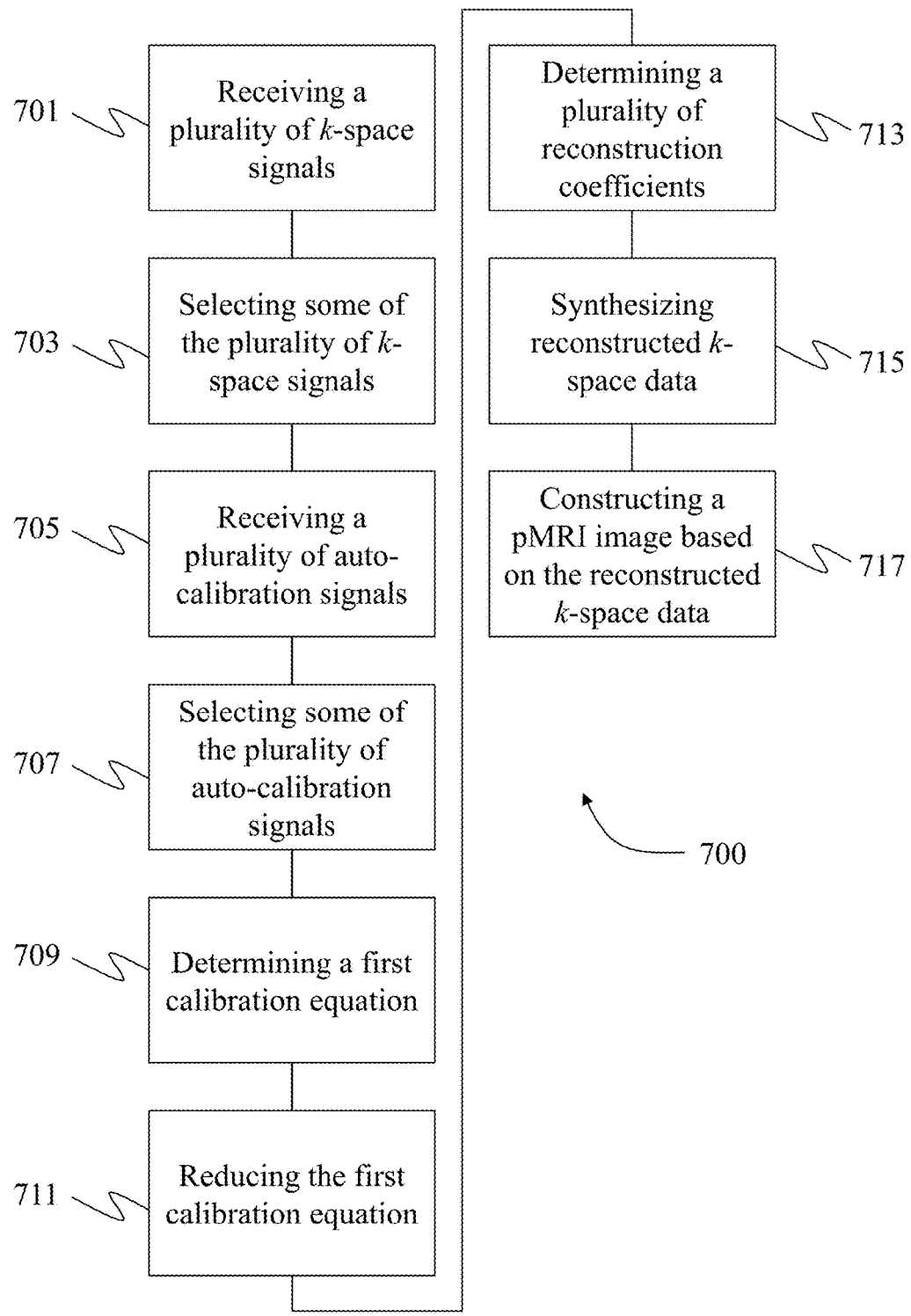
FIG. 14 is a flowchart showing one embodiment of a method according to the present disclosure.

One embodiment of the present disclosure is as a method for constructing a parallel magnetic resonance image. A flowchart showing this method is shown in FIG. 14. The parallel magnetic resonance image may be 2-Dimensional or 3-Dimensional. In some embodiments, the parallel magnetic resonance image may include a plurality of 2-Dimensional or 3-Dimensional images captured at various points in time to create a video (i.e., a 4-Dimensional image).

The method comprises the step of receiving 701, at a processor, a plurality of k-space signals. The signals may be received 701 from a pMRI machine or an electronic storage device containing k-space signals. K-space is the 2-Dimensional or 3-Dimensional Fourier transform of a measured magnetic resonance (MR) image measured. K-space signals may comprise complex values sampled during a magnetic resonance measurement, in a premeditated scheme controlled by a pulse sequence, i.e., an accurately timed sequence of radiofrequency and gradient pulses. K-space may refer to the temporary image space, usually a matrix, in which data from digitized signals are stored during data acquisition. Thus, k-space signals may comprise raw data used during image reconstruction.

Each k-space signal may correspond to a channel of a receiver coil. Receiver coils receive, and sometimes transmit, radio frequency (RF) signals in pMRI hardware. The MR signal in pMRI is produced by the process of resonance, which is the result of the receiver coils. The receiver coil may detect RF electromagnetic radiation produced by nuclear relaxation inside an imaging subject. The received 701 signal may comprise true EM radiation (i.e., radio waves). Receiver coils may be grouped into two classes: volume and surface coils.

Volume coils may be designed to provide a homogeneous RF excitation across a large volume. Many pMRI scanners include a built in volume coil to perform whole-body imaging, and smaller volume coils may be used for imaging the head and other extremities. The RF homogeneity of volume coils is highly desirable for transmit, but is less ideal when the region of interest is small. The large field of view of volume coils means that during receive they receive noise from the whole body, not just the region of interest.

Surface coils may be designed to provide a very high RF sensitivity over a small region of interest. These coils are often single or multi-turn loops that are placed directly over the anatomy of interest. The size of these coils can be optimized for the specific region of interest. Their small field of view makes them ideal for receive, as they only detect noise from the region of interest.

A channel may refer to a receiver coil pathway of a pMRI system. Channels may be independent, complete electronic chains required for processing information received from a receiver coil segment. For example, channels may comprise amplifiers, filters, analog-to-digital conversion circuitry, demodulation/mixer devices, and image processing capability. The output of each channel is generally a partial view of the entire subject being imaged, subsequently combined with output from the other channels to produce the final MR image.

Each k-space signal may comprise a combination of sample data corresponding to the parallel magnetic resonance image and sensitivity information of a channel.

The method further comprises the step of selecting 703, using the processor, a subset of the plurality of k-space signals. The plurality of k-space signals may be selected 703 using principal component analysis (PCA), or another suitable algorithm. For example, singular value decomposition (SVD), spectral decomposition, polar decomposition, and quadratic residue (QR) decomposition may also be suitable algorithms.

In one embodiment, the step of selecting 703 a subset of the plurality of k-space signals comprises:
a) defining, using the processor, a set of N vectors. N may equal the total number of channels associated with the plurality of k-space signals;
b) calculating, using the processor, a mean corresponding to each vector in the set of N vectors;
c) subtracting from each vector in the set of N vectors, using the processor, the calculated mean associated from its corresponding vector;
d) calculating, using the processor, a covariance matrix;
e) calculating, using the processor, a plurality of eigenvectors of the covariance matrix;
f) creating, using the processor, a compression matrix based on the plurality of eigenvectors; and
g) selecting, using the processor, a subset of the plurality of k-space signals by multiplying the plurality of k-space signals by the compression matrix.

The method further comprises the step of receiving 705, at the processor, a plurality of auto-calibration signals (ACS). ACS lines may be acquired along the direction orthogonal to that of the plurality of k-space signals. ACS lines may be acquired in other directions, such as parallel to the k-space signals. ACS lines may improve calibration and thus improve image quality but prolong imaging time. When the number of ACS lines is insufficient, aliasing artifacts are present in reconstruction along the undersampled direction.

The method further comprises the step of selecting 707, using the processor, a subset of the plurality of auto-calibration signals The step of selecting 707 may be performed in a similar manner as the step of selecting 703 a subset of the plurality of k-space signals. Other algorithms may be utilized.

The method further comprises the step of determining 709, using the processor, a first calibration equation. The first calibration equation may be associated with the selected auto-calibration signals and the selected k-space signals.

The method further comprises the step of reducing 711, using the processor, the first calibration equation. The reduced calibration equation has a lesser dimensionality than the first calibration equation. The reduction in dimensionality may refer to a reduction in the number of equations or variables under consideration. The first calibration equation may be reduced by randomly selecting a subset of the first calibration equation. The first calibration equation may also be reduced by multiplying the first calibration equation with a random projection matrix. For example, the random projection matrix may comprise elements from the following distribution:

$$R_{(i,j)} = \sqrt{3} \begin{cases} 1 & p = 1/6 \\ 0 & p = 2/3 \\ -1 & p = 1/6 \end{cases}$$

Other random projection matrices may be used. In some embodiments, deterministic matrices may be used that satisfy the restricted isometry property. The restricted isometry property characterizes matrices that are nearly orthonormal, at least when operating on sparse vectors. In particular, random Gaussian, Bernoulli, and partial Fourier matrices often satisfy the restricted isometry property with number of measurements nearly linear in sparsity level.

The method further comprises the step of determining 713, using the processor, a plurality of reconstruction coefficients. The plurality of reconstruction coefficients may be based on the reduced calibration equation. Each coefficient may correspond to a channel of the receiver coil. The plurality of reconstruction coefficients may be determined using a least-squares method. The method of least squares is an approach to an approximate solution of overdetermined systems, i.e., sets of equations in which there are more equations than unknowns. Least squares means that the overall solution minimizes the sum of the squares of the errors made in the results of every single equation. Other methods may be used.

In another embodiment, the plurality of reconstruction coefficients may be determined 713 using a cost function minimization algorithm. For example, the cost function minimization algorithm may calculate the plurality of reconstruction coefficients under a specified constraint such as the l1-norm or l2-norm. The $l^1$-Norm may be a vector norm defined for a vector:

$$x = \begin{bmatrix} x_1 \\ x_2 \\ \vdots \\ x_n \end{bmatrix}$$

with complex entries by $$|x|_1 = \sum_{r=1}^{n} |x_r|.$$

The $l^2$=Norm may be a vector norm defined for a complex vector:

$$x = \begin{bmatrix} x_1 \\ x_2 \\ \vdots \\ x_n \end{bmatrix}$$

by $$|x| = \sqrt{\sum_{k=1}^{n} |x_k|^2},$$

where $|x_k|$ denotes the complex modulus.

The plurality of reconstruction coefficients may also be based on a sensitivity of the receiver coil.

The method further comprises the step of synthesizing 715, using the processor, reconstructed k-space data. The reconstructed k-space data may be based on the plurality of reconstruction coefficients and received k-space signals.

The method further comprises the step of constructing 717, using the processor, a parallel magnetic resonance image based on the reconstructed k-space data.

One embodiment of the present disclosure is as a system for constructing a parallel magnetic resonance image. The system may comprise a parallel magnetic resonance imaging device. The pMRI device may have a plurality of receiver coils. Each receiver coil may have a plurality of channels.

The system may further comprise an image reconstruction device. The image reconstruction device may be in electronic communication with the parallel magnetic resonance imaging device.

The image reconstruction device may comprise an electronic storage device. The electronic storage device may be configured to contain data corresponding to a parallel magnetic resonance image.

The image reconstruction device may also comprise a processor. The processor may be in electronic communication with the electronic storage device and the parallel magnetic resonance imaging device.

The processor may be configured to receive a plurality of k-space signals from the parallel magnetic imaging device. Each k-space signal may correspond to a channel of a receiver coil. Each k-space signal may comprise a combination of sample data corresponding to the parallel magnetic resonance image and sensitivity information of a channel.

The processor may also be configured to select a subset of the plurality of k-space signals. The processor may be configured to select some of the plurality of k-space signals using principal component analysis.

The processor may also be configured to receive a plurality of auto-calibration signals from the parallel magnetic imaging device or electronic storage device.

The processor may also be configured to select a subset of the plurality of auto-calibration signals.

The processor may also be configured to determine a first calibration equation associated with the selected auto-calibration signals and the selected k-space signals.

The processor may also be configured to reduce the first calibration equation to a reduced calibration equation having a lesser dimensionality than the first calibration equation. The processor may be configured to reduce the first calibration equation by randomly selecting a subset of the first calibration equation. The processor may also be configured to reduce the first calibration equation by multiplying the first calibration equation with a random projection matrix. the random projection matrix may comprise elements from the following distribution:

$$R_{(i,j)} = \sqrt{3} \begin{cases} 1 & p = 1/6 \\ 0 & p = 2/3 \\ -1 & p = 1/6 \end{cases}$$

The processor may also be configured to determine a plurality of reconstruction coefficients based on the reduced calibration equation. Each reconstruction coefficient may correspond to a channel of the receiver coil. The processor may be configured to determine the plurality of reconstruction coefficients based on a sensitivity of the receiver coil. The processor may also be configured to determine the plurality of reconstruction coefficients using a cost function minimization algorithm. The cost function minimization algorithm may cause the processor to calculate the plurality of reconstruction coefficients under a specified constraint.

The processor may also be configured to synthesize reconstructed k-space data based on the plurality of reconstruction coefficients and received k-space signals.

The processor may also be configured to construct a parallel magnetic resonance image based on the reconstructed k-space data.

One embodiment of the present disclosure can be described as a random projection method. This embodiment can reduce the dimension of the over-determined equations in calibration and thus save computational time. This embodiment can be integrated with existing channel reduction methods such as PCA and other channel reduction methods.

For example, PCA performs the Eigen-decomposition on the covariance matrix of the channel data and removes the components that correspond to the smallest eigenvalues. The resulting fewer combined channels corresponding to the largest eigenvalues are used for reconstruction such that the reconstruction time is reduced.

PCA is based on the statistical representation of a random variable. Generally, there are six steps to follow in performing PCA. Some versions of PCA may have fewer or additional steps. The following is a description of an exemplary PCA process.

Step 1. Define the input data set of PCA. The data set is composed of N vectors $X_1, \ldots, X_N$. Each vector is a random vector population X, where $X=(x_1, \ldots, x_n)^T$ and T implies transposition. Each vector has the same dimension. For example, the PCA may be applied to the data simultaneously acquired from an N-channel coil array. These N sets of data may be sampled and arranged in the same fashion to form the N vectors for PCA. The dimension of every vector is equal to the number of sampling points.

Step 2. Produce vectors with means of zero. In this step, each vector is adjusted by subtracting its mean; that is $$\hat{X} = X - \frac{\sum_{i=1}^{n} x^i}{n}.$$

Step 3. Calculate the covariance matrix C. The components of C, denoted by $C_{ij}$, represent the covariances between the random variable components $\hat{X}_i$ and $\hat{X}_j$.

$$c_{ij} = \text{cov}(\hat{X}_i, \hat{X}_j) = \frac{\text{conj}(\hat{X}_i^T)\hat{X}_j}{n-1}$$

where conj(•) means conjugate. The variance of a component indicates the spread of the component values around its mean value. If two components $\hat{X}_i$ and $\hat{X}_j$ of the data are uncorrelated, their covariance ($c_{ij}=c_{ji}=0$) is zero. The covariance matrix is, by definition, always symmetric.

Step 4. Calculate the eigenvectors and eigenvalues of the covariance matrix.

Step 5. Choose components and form a compression matrix. Let A be the matrix consisting of eigenvectors of the covariance matrix as the column vectors; A is called the transformation matrix. Instead of using all the eigenvectors of the covariance matrix, the L last eigenvectors can be used, corresponding to L largest eigen-values. These L eigenvectors form a new matrix $A_L$, and $A_L$ is the compression matrix that can combine N vectors to L vectors.

Step 6. Generate the new data set. In this step, simply multiply the original data set by the compression matrix. $(Y_1, Y_2, \ldots, Y_L)=(X_1, X_2, \ldots, X_N)A_L$, where $(Y_1, Y_2, \ldots, Y_L)$ is the compressed data set.

The channel reduction method can be PCA, but other channel reduction methods can be used.

In auto-calibrated reconstruction, generally there are two steps: the calibration step and the synthesis step. For example, with GRAPPA, during the calibration step, acquired ACS data is used to calibrate the GRAPPA reconstruction coefficients in k-space. Specifically, the k-space data points that should be skipped during the accelerated scan are assumed to be approximately equal to a linear combination of the acquired under-sampled data in the neighborhood from all coils, which can be represented as $$S_j(k_y + r\Delta k_y, k_x) = \sum_{l=1}^{L} \sum_{b=B_1}^{B_2} \sum_{h=H_1}^{H_2} w_{j,r}(l, b, h) \times S_l(k_y + bR\Delta k_y, k_x + h\Delta k_x) \quad [\text{Eq. 1}]$$

where $S_j$ on the left-hand side denotes the target data that should be skipped but is acquired for the calibration purpose, and $S_l$ on the right-hand side is the source k-space signals that should originally be acquired, both in the ACS region. Here w denotes the coefficient set, R represents the outer reduction factor (ORF), r is the offset, j is the target coil, l counts all coils, b and h transverse the acquired neighboring k-space data in $k_y$ and $k_x$ directions respectively, and the variables $k_x$ and $k_y$ represent the coordinates along the frequency- and phase-encoding directions, respectively.

The GRAPPA calibration step can be simplified as a matrix equation $$b_{m \times 1} = A_{m \times n} x_{n \times 1} \quad [\text{Eq. 2}]$$

where A represents the matrix comprised of the source data, b denotes the vector of the additional acquired target data for calibration, and x represents the linear combination coefficients and/counts for all coils and all possible offsets. In general, the coefficients depend on the coil sensitivities and are not known a priori. In calibration, the goal is to find the unknown x based on the matrix Eq. [2]. The vector b and matrix A include data at all locations of the ACS region to find the best GRAPPA coefficients x. In general, the least-squares method is commonly used to calculate the coefficients:

$$\hat{x} = \min_{x} \|b - Ax\|^2 \quad [\text{Eq. 3}]$$

Many ACS data points are usually acquired to set up Eq. [2], which means the problem is well over-determined. In this case, the solution is given by:

$$x = (A^H A)^{-1} (A^H b) \quad [\text{Eq. 4}]$$

It is worth mentioning that there are other methods (e.g., LU decomposition and iterative conjugate gradient) to solve Eq. [2]. They may be more efficient than the pseudo-inverse method in Eq. [4], depending on the scale of the equation.

During the synthesis step, based on the shift-invariant assumption, the same equation Eq. [2] is used with the same x obtained from Eq. [4], but to obtain the unknown b using the data from the k-space data outside the ACS region for A. By this means, the missing data b is estimated by the linear combination of the acquired data in A and the full k-space data can be used to obtain the image of each channel. The final image is reconstructed using the root sum of squares of the images from all channels.

To reduce the dimension of the calibration Eq. [2], a random matrix R of k×m is defined to project the original m-dimensional data onto a k-dimensional (k<<m) subspace with a dimension reduction factor m/k. The random matrix is then multiplied on both sides of the calibration Eq. [2]:

$$R_{k \times m} b_{m \times 1} = R_{k \times m} A_{m \times n} x_{n \times 1} \quad [\text{Eq. 5}]$$

where k is the reduced dimension. Applying the random projection (RP) using Eq. [5] is equivalent to linearly combining a subset of equations in a random fashion to form a new reduced set of equations or randomly selecting a subset of equations. The range for k may be 1.1 to 4 times of n. k also should be smaller than m. Other values for k may be used.

x may be calculated by the minimization of the $l_2$ norm $$\hat{x} = \min_{x} \|R_{k \times m} b_{m \times 1} - R_{k \times m} A_{m \times n} x_{n \times 1}\|_2^2 \quad [\text{Eq. 6}]$$

However, it is not limited to minimizing the $l_2$ norm. x can also be calculated by the minimization of the $l_1$ norm:

$$\hat{x} = \min_{x} \|R_{k \times m} b_{m \times 1} - R_{k \times m} A_{m \times n} x_{n \times 1}\|_1 \quad [\text{Eq. 7}]$$

Synthesis: The missing k-space data $\hat{b}$ can be calculated by a linear combination as follows:

$$\hat{b} = \tilde{A} \hat{x} \quad [\text{Eq. 8}]$$

where $\tilde{A}$ represents the matrix comprised of the neighboring acquired data corresponding to the missing data, $\hat{x}$ denotes the calculated linear combination coefficients in Eq. [5].

After the synthesis step, all, or nearly all, the k-space data is obtained. The image from each can be acquired by applying the following two dimensional inverse Fourier transform:

$$I(p, q) = \frac{1}{PQ} \sum_{x=0}^{P-1} \sum_{y=0}^{Q-1} e^{2\pi i (xp/P + yq/Q)} k(x, y) \quad [\text{Eq. 9}]$$

Where I is the reconstructed image, p, q are the indexes for each pixel of the reconstructed image. x, y are the indexes for the k-space data. P and Q represent the dimension of the k-space data.

Figure 1:
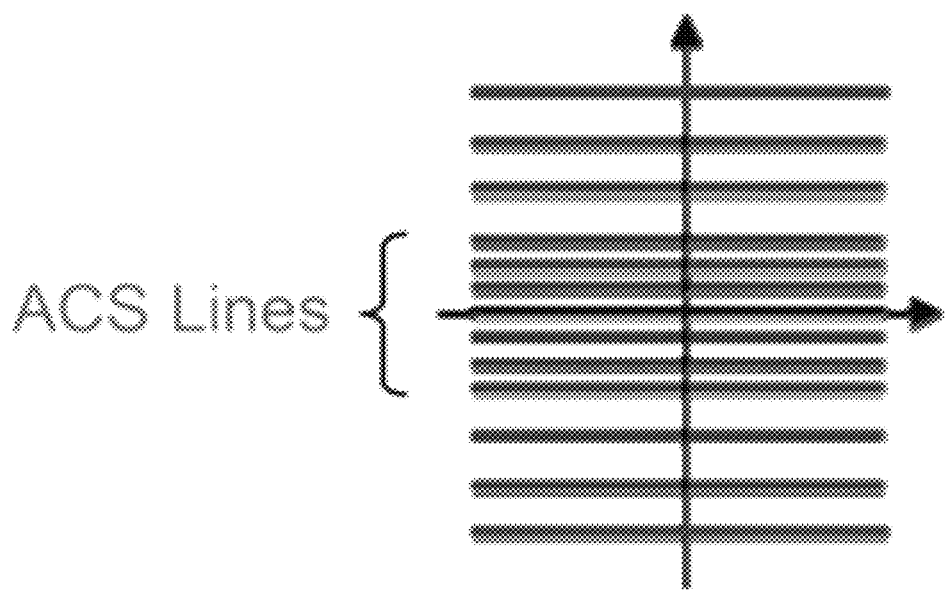
FIG. 1 is an illustration of Cartesian scanning trajectory in k-space.

In a first embodiment, the random projection is performed alone. In this embodiment, the method is applied to MR data collected with a Cartesian trajectory. FIG. 1 shows a diagram of a variable density (VD) Cartesian scan in k-space, wherein the outermost regions of k-space are scanned at lower density than the central regions. The higher-density scans in the central region labeled "ACS Lines" correspond to the auto-calibration signal data that is used to estimating the fitting coefficients. FIG. 1 is an illustration of 2D acquisition (phase and frequency encodings). The method is directly applicable to 3D acquisition (slice, phase, and frequency encodings).

Figure 2:
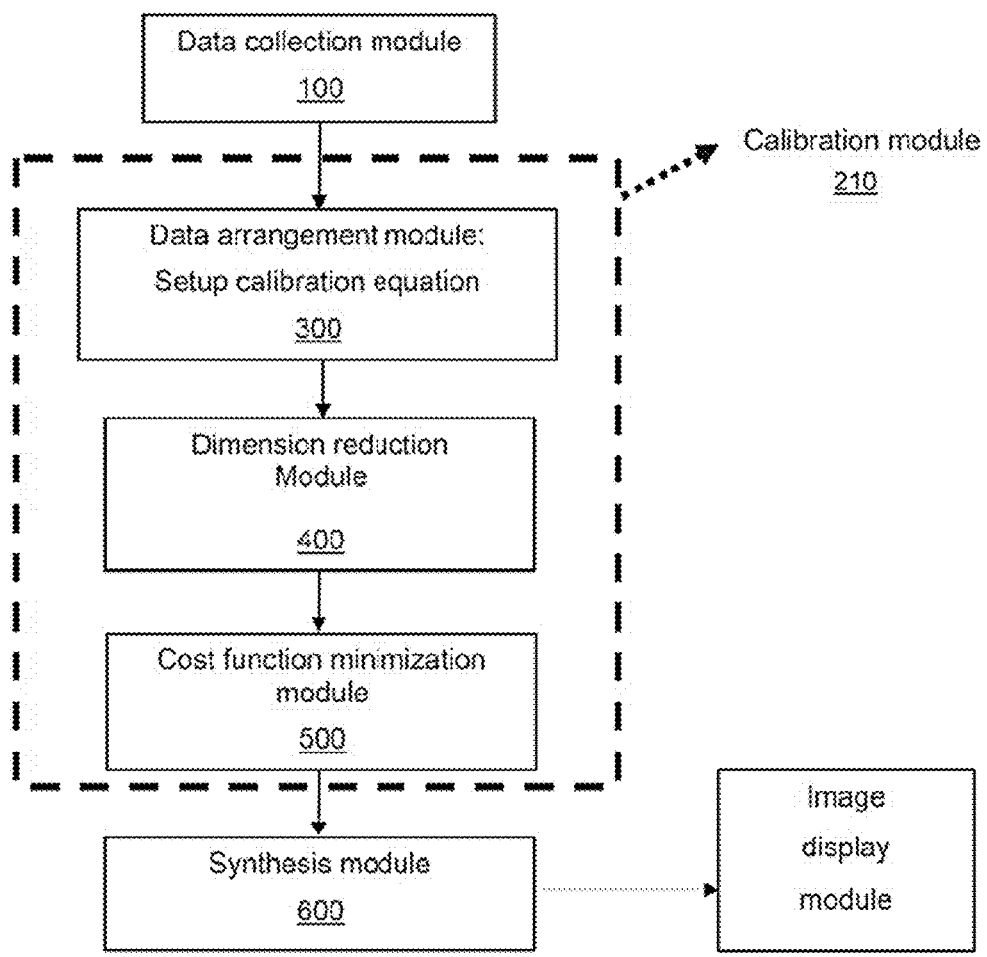
FIG. 2 is a block diagram showing one embodiment of the present disclosure.

A block diagram of an apparatus according to the first embodiment of the disclosure is shown in FIG. 2. A data collection module 100, such as a parallel MRI system, collects k-space data. A data arrangement module 300 selects data from the ACS lines according to different modes and different channels and setup the calibration equation. The random projection module 400 reduces the dimension of the calibration equation. A cost function minimization module 500 calculates the fitting coefficients that best fit the calibration equation under a specified constraint. The constraint can either be the $l_1$-norm constraint or the $l_2$-norm constraint. Modules 300, 400, 500 together comprise the calibration module 210 in this first embodiment. The fitting coefficients are used in the synthesis module 600. The output data from module 600 is the reconstructed full k-space data. These full k-space data is converted to the image that can be displayed in the image display module.

Figure 3:
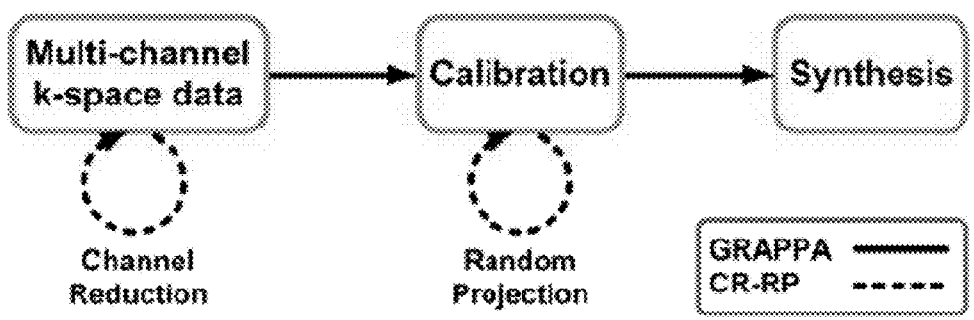
FIG. 3 is a flow chart showing the CR-RP-GRAPPA embodiment of the present disclosure.

Although channel reduction and random projection are both linear dimensionality reduction methods, they have different objectives and properties after the reduction. For example, in PCA (a channel reduction method), the variance is to be maximized, which is ideal for channel reduction. While in random projection, the data distance needs to be maintained, which is ideal for reducing linear equations without changing the least squares solutions. In addition, the two methods are exploited at different stages of auto-calibrated reconstruction. For example, PCA is performed for channel reduction (CR) before the reconstruction, and random projection is done during the GRAPPA calibration step of reconstruction. The relationship is illustrated in FIG. 3. FIG. 3 shows a flow chart of the CR-RP-GRAPPA embodiment of the present disclosure. CR can be performed on the multi-channel k-space data in the first step before further processing. The channel reduction method and random projection method are performed at different steps and can be integrated to further accelerate auto-calibrated reconstruction methods, such as GRAPPA and SPIRiT.

Figure 4:
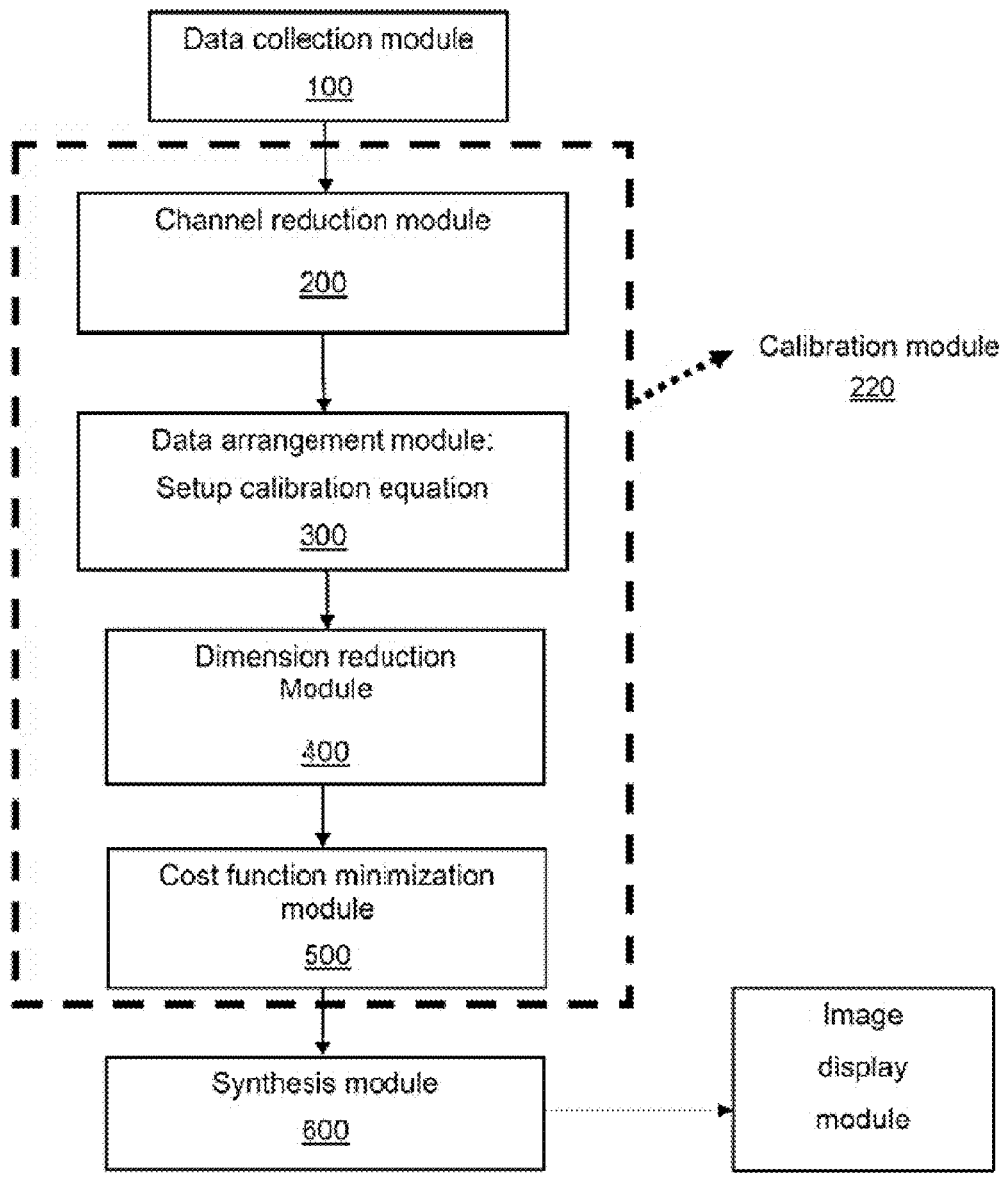
FIG. 4 is a block diagram of one embodiment of the present disclosure integrated with channel reduction (CR)

A block diagram of an apparatus according to a second embodiment of the invention is shown in FIG. 4. This embodiment integrates both PCA and random projection to significantly reduce the computational cost of GRAPPA. A data collection module 100, such as a parallel MRI system, collects k-space data. A channel reduction module 200 reduces the large number of physical channels to fewer virtual ones. After that, a data arrangement module 300 selects data from the ACS lines according to different modes and different channels and setup the calibration equation. The random projection module 400 reduces the dimension of the calibration equation. A cost function minimization module 500 calculates the fitting coefficients that best fit the calibration equation under a specified constraint. The constraint can either be the $l_1$-norm constraint or the $l_2$-norm constraint. Modules 200, 300, 400, 500 comprise the calibration module 220 in the second embodiment. The difference between the second embodiment and first embodiment is the channel reduction module 200 being integrated into the calibration module.

Figure 5:
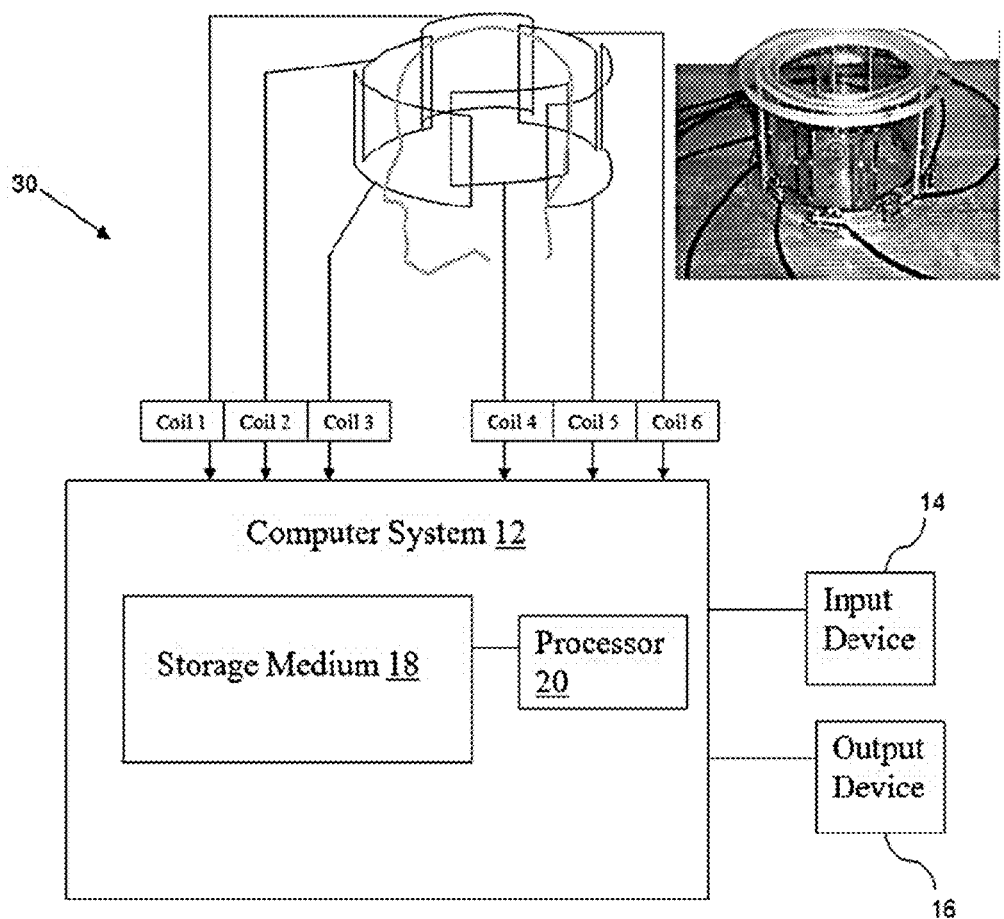
FIG. 5 is a diagram of a pMRI device and associated computer acquisition and processing systems.

Embodiments of the present disclosure, which are exemplified in the following examples, can be implemented on a computer system 12 connected to a pMRI system (FIG. 5). In FIG. 5, the photo in the inset shows a set of receiver channels in a coil similar to those shown diagrammatically in the line drawing. The computer system 12 has an input device 14, an output device 16, storage medium 18, and a processor 20 (FIG. 5). Possible input devices 14 include a keyboard, a computer mouse, a touch screen, and the like. Output devices 16 include various display devices including a cathode-ray tube (CRT) computer monitor, a liquid-crystal display (LCD) computer monitor, and the like, as well as printing devices such as an ink jet printer, a laser printer, and the like. Storage media 18 include various types of memory such as a hard disk, RAM, flash memory, and other magnetic, optical, physical, or electronic memory devices. The processor 20 is any computer processor or processors for performing calculations and directing other functions for performing input, output, calculation, and display of data related to the inventive methods. Embodiments of the present disclosure may comprise instructions and data that are stored on the storage medium 18. In addition, embodiments of the present disclosure may operate on data collected from the attached pMRI system 30.

EXAMPLE 1

In this example, the dimension of GRAPPA calibration equation is reduced using random projection. In GRAPPA calibration, the objective is to reduce the dimension of Ax and b such that their relative distance $\|Ax-b\|_2$ is preserved. The random projection is able to serve this purpose based on the JL lemma.

With the matrix R below, there is a high probability to maintain the important information in the lower dimension space after the projection. The solution to the reduced set of equations is approximately the same as the original one because for any $x_{n\times l}$, $$\|R_{k\times m}A_{m\times n}x_{n\times l}-R_{k\times m}b_{m\times l}\|_2 \approx \|A_{m\times n}x_{n\times l}-b_{m\times l}\|_2 \qquad [\text{Eq. 10}]$$

provided k is not too small. The range for k may be 1.1 to 4 times of n. k also should be smaller than m. Other values for k may be used.

In contrast to PCA, the computation complexity of random projection is rather low, requiring kin multiplications in general. The complexity can be further reduced by carefully choosing the distribution. Although most random matrices would be applicable, here a matrix R that randomly selects the equations or R whose elements are drawn from I.I.D. distribution with the following density is used:

$$R_{(i,j)} = \sqrt{3}\begin{cases} 1 & p=1/6 \\ 0 & p=2/3 \\ -1 & p=1/6 \end{cases}.$$

This random projection satisfies the JL lemma. Other random projections may also satisfy the JL lemma. Such a simple and sparse construction in R incurs a large saving in computational cost, because only a single multiplication and very few additions are needed when computing the projection.

The reduced dimension k directly affects the computational complexity of calibration. With random projection, the computational cost of the calibration process is greatly reduced. Instead of solving an m×n equation, a k×n equation is solved, where k<<m. Here k is heuristically chosen to be 2 to 4 times n. That is, for the same number of unknowns n, the number of equations have been reduced to be about 2 to 4 times of that of unknowns. The exact computational savings depend on the specific problem using GRAPPA. For example, if k=2n is assumed, and the commonly used parameters for 2D GRAPPA (e.g., 32 ACS with 8 channels), then the size of the equation is reduced from 8,192×416 in Eq. [3] to 832×416 in Eq. [5]. The calibration process has a saving of approximately 10 times. With such a saving, the ratio between the computation time of the calibration and synthesis processes is reduced from 16.0 to 2.3. Compared with the conventional GRAPPA, the random projection brings in a total saving of 5.1 times in computational cost. If more data is involved in GRAPPA as in the cases of 3D reconstruction and massive array coils, greater savings are expected.

The computational benefit of the Example 1's random projection method for GRAPPA was evaluated on three scanned datasets. The first axial brain dataset was acquired on a GE 3T scanner (GE Healthcare, Waukesha, Wis.) with an 8-channel head coil using a 2D spin echo sequence (TE/TR=11/700 ms, matrix size=256×256, FOV=220 mm×220 mm). The second dataset was acquired on a Philips Ingenia 3T scanner with 12-channel head coil using a 3D Fast Field Echo sequence (TE/TR=4.6/25 ms, matrix size=239×239×83, FOV=240 mm×240 mm×130 mm). In the third dataset, a set of axial brain data was acquired on a Siemens 3T scanner (Siemens Trio, Erlangen, Germany) with a 32-channel head coil using a 2D gradient echo sequence (TE/TR=2.29/100 ms, flip angle=25, matrix size=256×256, slice thickness=3 mm, FOV=240 mm×240 mm).

These datasets were acquired in full and the square-root of sum-of-squares (rSOS) of the images from fully sampled data of all coils was used as the reference. The full k-space data was manually undersampled, retrospectively, to simulate the accelerated acquisition for GRAPPA. The GRAPPA reconstructions were compared with and without random projection to demonstrate the computational savings of Example 1's random projection method. In particular, the two approaches were compared when the same amount of ACS data was used as well as when both have the same computational complexity but with reduced ACS data for conventional GRAPPA. The reconstruction quality was evaluated both visually and quantitatively using the normalized mean squared error (NMSE) with the reference image as the gold standard. The computational savings was measured in terms of both the computational complexity calculated analytically as the total number of multiplications and the computation time measured in CPU time. Due to the random nature of the proposed method, the NMSE and CPU time were both obtained from the average results of 5 executions. For the proposed random projection method, a factor $\lambda=k/n>1$ was defined, which represents how much the new equation is over-determined after dimensionality reduction. The smaller the $\lambda$ is, the less the equation is over-determined and the less the computation is needed. For the 32-channel dataset, random projection was also combined with channel reduction methods. Specifically, the PCA channel reduction method was used to compress the 32 channels to fewer source channels and target channels (5-8), and then applied the proposed random projection method to GRAPPA reconstruction.

All methods were implemented in MATLAB (Mathworks, Natick, Mass.) and run on a PC with 3.4 GHz CPU and 16 GB memory. A software implementation of the random projection method is shown in the appendix.

Figure 6:
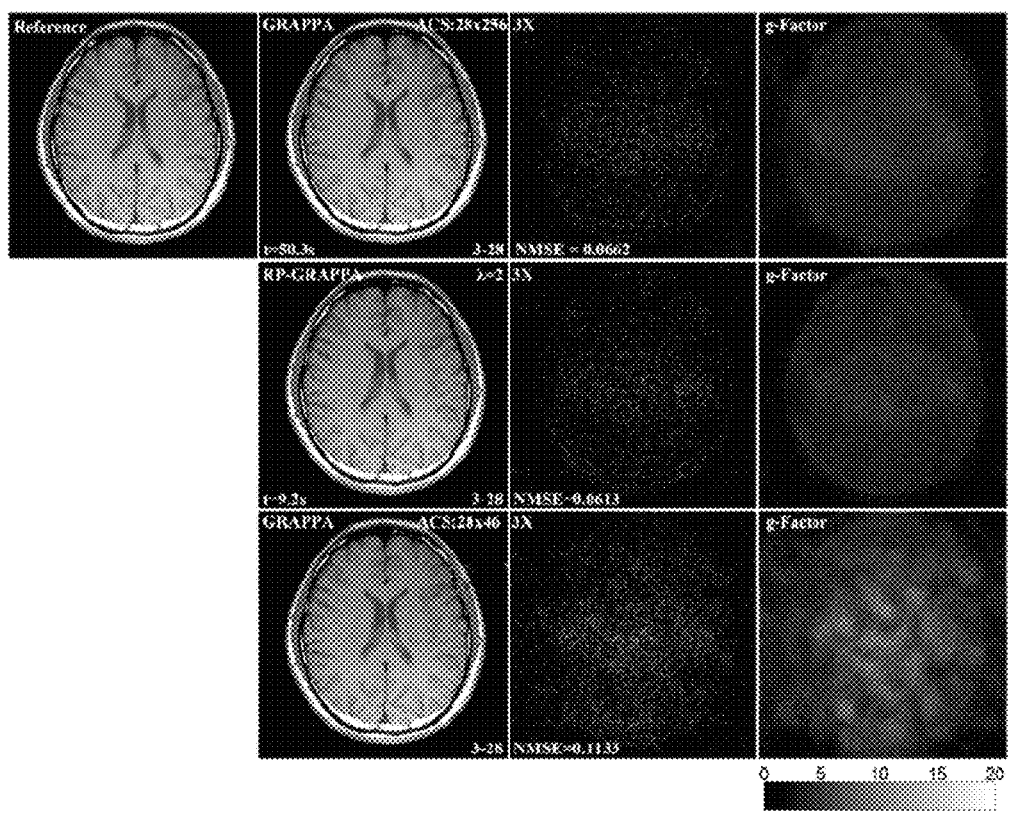
FIG. 6 is a set of axial brain images reconstructed from a set of eight-channel data with an outer reduction factor (ORF) of 3 and 28 ACS lines using GRAPPA and random projection (RP)-GRAPPA.

The computational saving of random projection on GRAPPA (RP-GRAPPA) was evaluated for 2D reconstruction using the first dataset. The data were undersampled along the phase encoding direction with an ORF of 3 with 28 ACS lines. Both GRAPPA and RP-GRAPPA were used to reconstruct the final image with the number of blocks $d_y=4$ and the number of columns $d_x=15$. The CPU times of GRAPPA and RP-GRAPPA were 104.44 s and 16.48 s, respectively, and their ratio was $T_{GRAPPA}/T_{RP-GRAPPA} \approx 6.3$. Such a saving in computation time roughly agrees with the theoretical analysis. In addition, the number of columns in ACS data were reduced for GRAPPA reconstruction to make the computation time to be about the same as that of RP-GRAPPA. The reconstructions, their corresponding difference images with the reference, and the g-factor maps are shown in FIG. 6. The normalized mean squared errors (NMSE) are 0.0662 for GRAPPA, 0.0613 for RP-GRAPPA, and 0.1133 for ACS-reduced GRAPPA. The proposed random projection method was able to reduce the GRAPPA reconstruction time by a factor of 6.3 without compromising the image quality. Equivalently, the proposed method was able to improve the GRAPPA reconstruction quality with the same computation time. The corresponding difference images are shown on the middle column of FIG. 6 (3× amplification) and g-factor maps on the right column. The RP-GRAPPA embodiment of the present disclosure can achieve a similar reconstruction quality to GRAPPA with much less CPU time or take about the same CPU time as GRAPPA but with better SNR.

Figure 7:
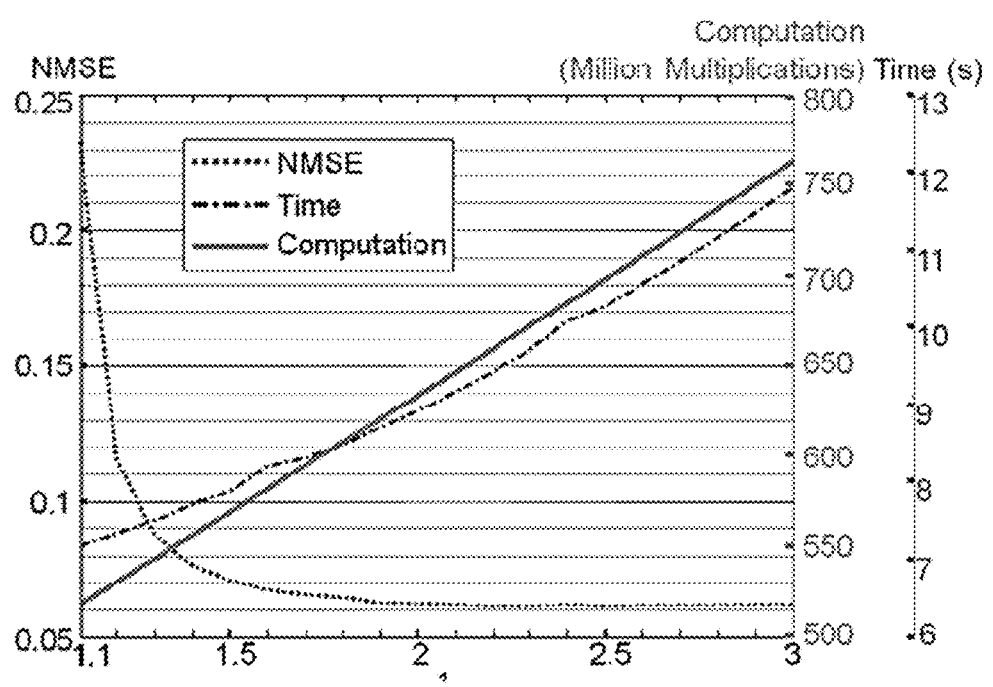
FIG. 7 is a chart showing normalized mean squared error (NMSE) and CPU time of RP-GRAPPA versus λ (8-channel dataset; ACS=28, ORF=3, block=4, column=15)

Also studied is how the number of equations after the random projection affects the GRAPPA reconstruction quality. To study this effect, $\lambda$ was increased from 1.1 to 3, with a step size of 0.1. In consideration of the sparse distribution of random projection matrix R, the sparsity-control parameter p was changed from 0.05 to 0.5. The test results show that the sparsity-control parameter p does not affect the NMSE of reconstruction results. Without loss of generality, p=0.2 was fixed in the experiments. FIG. 7 is a chart showing NMSE and CPU time of RP-GRAPPA versus $\lambda$ (8-channel dataset; ACS=28, ORF=3, block=4, column=15). The CPU time curve shows similar linear increasing trend as the theoretical result. It was seen that the NMSE decreases rapidly (approximately in exponential) as $\lambda$ increases and becomes sufficiently low for $\lambda>2.5$.

Also calculated was the overall (both calibration and synthesis) computation complexity of RP-GRAPPA under different $\lambda$. CPU time was also recorded. The results are shown on the same plot as the NMSE curve in FIG. 7. From the results, it is shown that the computation complexity increases linearly as $\lambda$ increases. The almost-linear trend of CPU time with respect to $\lambda$ is consistent with that of the computation complexity.

FIG. 7 suggests that $\lambda$ has to be sufficiently large to maintain the reconstruction quality. When $\lambda$ increases, reconstruction error is suppressed exponentially, while the CPU time increases only linearly. For $1.5<\lambda<3$, the NMSE is sufficiently low, while the CPU time also remains short. The optimal range for $\lambda$ to balance the tradeoff between NMSE and CPU is seen to be between 1.5 and 3. However, other values for $\lambda$ may be used while still receiving suitable results.

Figure 8:
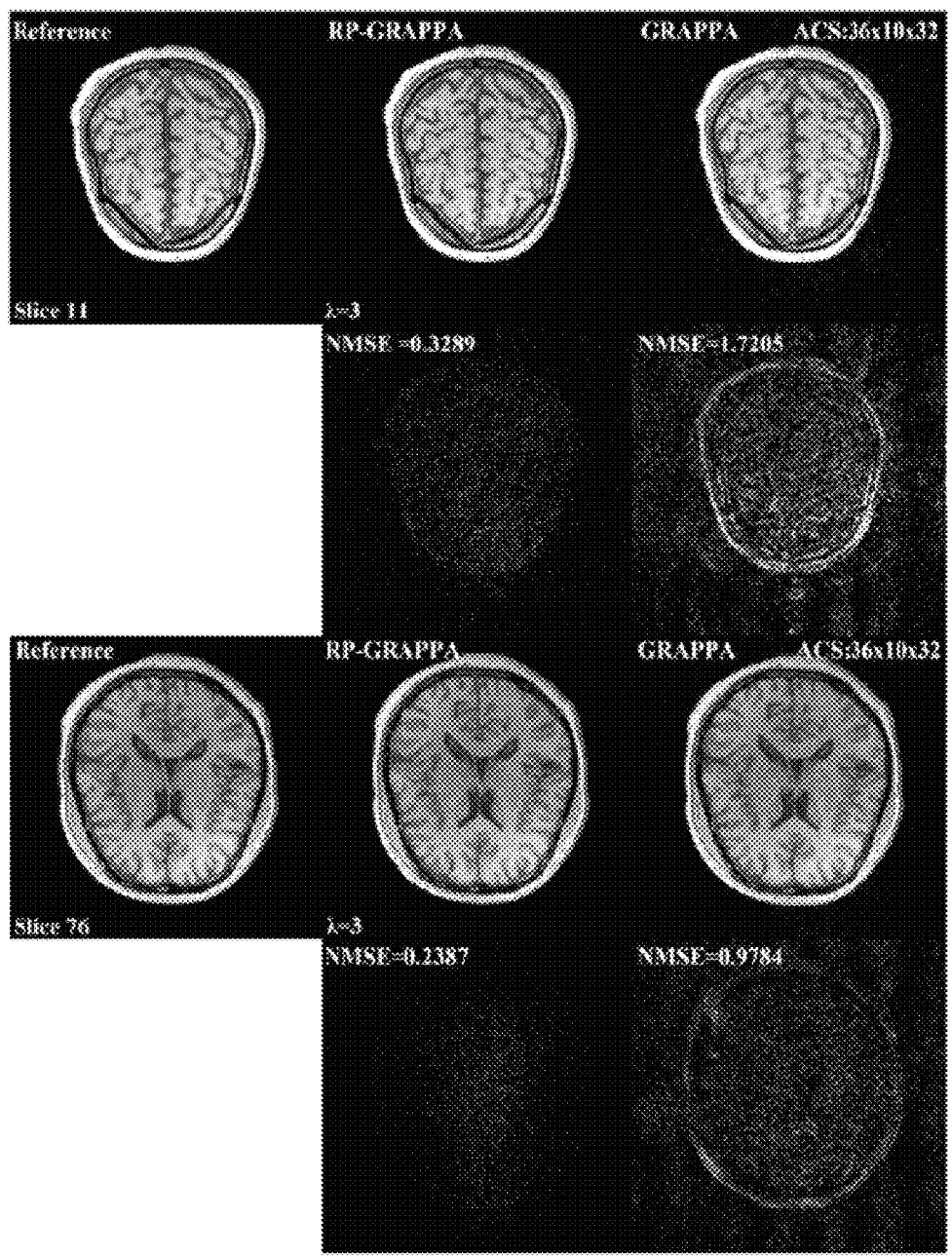
FIG. 8 is a set of 3D-reconstructions images using GRAPPA and RP-GRAPPA with 2D undersampling (12 channel dataset; ACS=36×32, ORF=2×2, block=4×4, column=15)

In 3D reconstruction, the calibration process becomes even more time consuming due to the larger amount of data involved in the equation. A second dataset was used to evaluate the computational savings in 3D GRAPPA reconstruction. For this 12-channel dataset with a matrix size of 239×239×83, an ORF of 2×2 with 36×32 ACS lines was used. The number of blocks $d_y$ and $d_z$ were both 4, and the number of columns $d_x$ was 13. The central 101 columns (frequency encodings) of these ACS lines were initially used for calibration. Due to the high computation complexity involved such a large set of 3D calibration data, the calibration process was performed for only the first mode and the first channel to estimate the time. Such a single step of calibration takes CPU times of 108 s and 1852 s for 3D RP-GRAPPA and 3D GRAPPA, respectively. This shows that the proposed random projection brings a saving of about 17 times in 3D GRAPPA calibration time. The total calibration times were estimated to be 17.5 hours and 296 hours for 3D RP-GRAPPA and 3D GRAPPA, respectively. Due to such inhibiting calibration time for 3D GRAPPA without random projection, the ACS data was reduced to include only 15 columns for conventional GRAPPA such that the resulting calibration time is approximately the same as that of RP-GRAPPA with 101 columns. The 3D GRAPPA and 3D RP-GRAPPA reconstructions were compared with their corresponding references. FIG. 8 shows 3D-reconstructions images using GRAPPA and RP-GRAPPA with 2D undersampling (12 channel dataset; ACS=36×32, ORF=2×2, block=4×4, column=15). All ACS columns are used in RP-GRAPPA and only 10 columns are used in GRAPPA to make their computational complexities about the same. The 3D RP-GRAPPA embodiment can achieve better SNR than 3D GRAPPA when both methods take about the same time.

FIG. 8 shows four slices of the reconstructions. The results suggest that 3D GRAPPA reconstruction has poorer SNR than 3D RP-GRAPPA due to fewer ACS columns used in consideration of computation time.

A third dataset with 32 channels was used to demonstrate the benefit of integrating channel reduction with random projection for GRAPPA reconstruction (PCA-RP-GRAPPA), where PCA was used for channel reduction. The data was manually undersampled with ACS=48, ORF=5 (net acceleration of 2.84). The number of columns $d_x$ was 15. For PCA-based channel reduction, the source channel number and target channel number were chosen to be $N_{sch}$=24 and $N_{tCh}$=8, respectively. The channel reduction factor was $N_c/N_{tch}$=4. The results of PCA-RP-GRAPPA were compared with those of RP-GRAPPA and conventional GRAPPA in terms of visual quality, NMSE, and reconstruction time.

Figure 9:
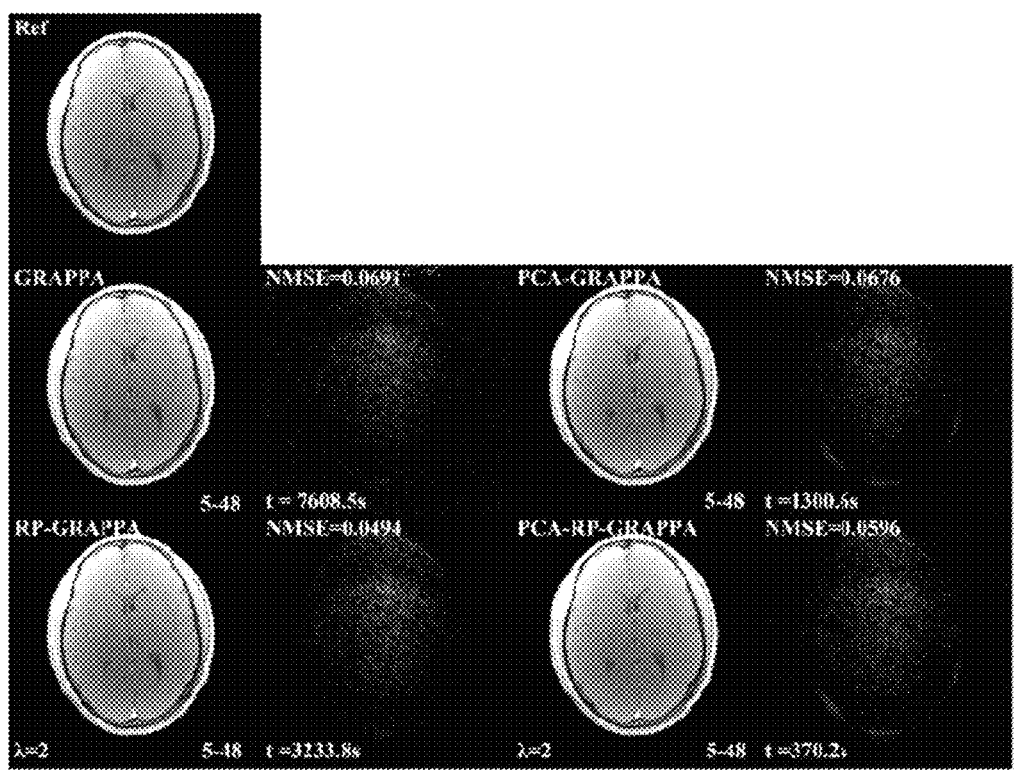
FIG. 9 is a set of brain images reconstructed from a set of 32-channel data with an ORF of 5 and 48 ACS lines using GRAPPA, RP-GRAPPA, PCA-GRAPPA, and PCA-RP-GRAPPA.

FIG. 9 shows brain images reconstructed from a set of 32-channel data with an ORF of 5 and 48 ACS lines using GRAPPA, RP-GRAPPA, PCA-GRAPPA, and PCA-RP-GRAPPA. The PCA channel reduction factor is 32-channel/8-channel=4. The random projection method integrates with existing channel reduction methods and shows an even smaller CPU time.

FIG. 9 shows the comparison with different $\lambda$. It is seen that when the number of channels is large, random projection alone is not as effective as channel reduction in reducing the computation time without compromising the image quality. However when the random projection and channel reduction are combined, the reconstruction time can be significantly reduced. For example, with $\lambda$=1.5, a factor up to 28 in saving can be achieved for the GRAPPA reconstruction time.

It is seen that there are at least three ways to reduce the number of calibration equations in order to reduce the computational complexity. The most straightforward way is to reduce the amount of ACS data. As shown above, a large reduction usually leads to degradation in reconstruction quality. The other two approaches are channel reduction and random projection. As shown above, a channel reduction method is very effective when there are a large number of channels. However, very little savings can be achieved when only a few physical channels are used. This is because the channel reduction method reduces the data redundancy cross channels only. To this end, the present disclosure's random projection method complements the channel reduction method for a large saving in computation because it reduces the redundancy among the calibration equations. The reason that PCA is appropriate only for channel reduction is that its own computational complexity is large when the size of the data becomes large. On the other hand, random projection is effective only when the dimension of the data is very high, and is thereby not effective in channel reduction.

Figure 10:
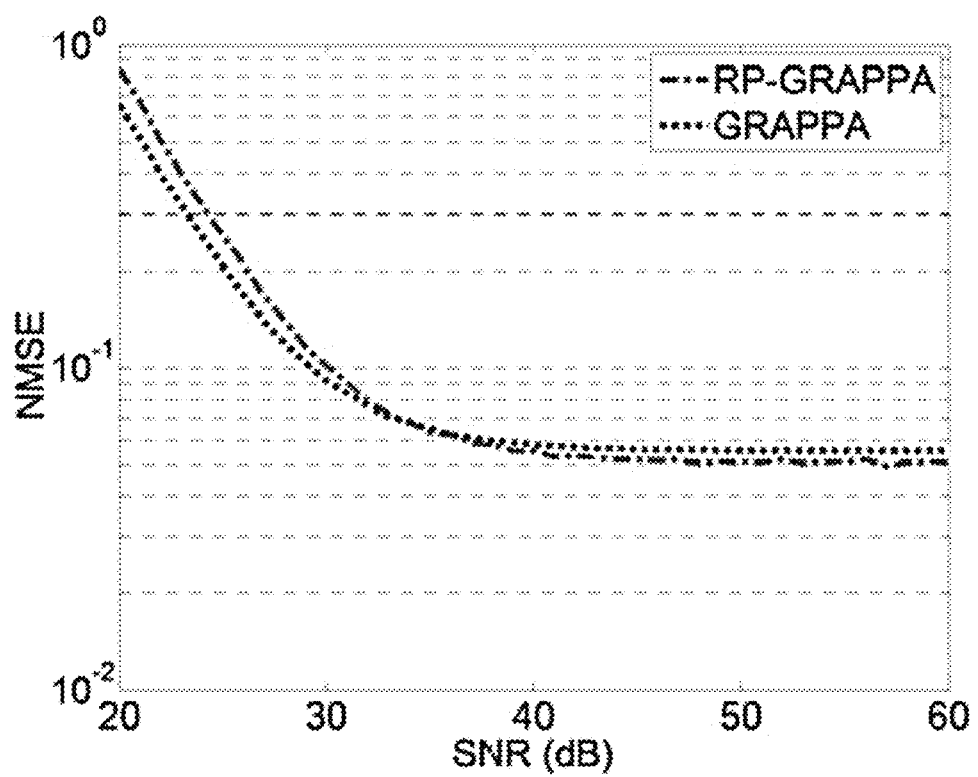
FIG. 10 is a chart showing the NMSEs of RP-GRAPPA and GRAPPA versus SNR (8 channel dataset; ACS=48, ORF=3, block=4, column=11, λ=2)

When $\lambda$ is sufficiently large, the NMSEs of the reconstructions with random projection are usually lower than those without. The NMSE curve in FIG. 7 shows that NMSE tends to increase slightly when $\lambda$ is larger than 2.3. This is because random projection has denoising capability at a certain level. When the error primarily comes from the noise in b of Eq. [3], random projection is able to reduce the error. In order to understand the observation more comprehensively, the NMSEs of GRAPPA and RP-GRAPPA are compared at different levels of signal-to-noise ratio (SNR), where white Gaussian noise is added onto the acquired k-space data (assumed to be noise-free) of the first dataset to simulate different SNRs. The results of this comparison are shown in FIG. 10. FIG. 10 shows the NMSEs of RP-GRAPPA and GRAPPA versus SNR (8 channel dataset; ACS=48, ORF=3, block=4, column=11, $\lambda$=2). The RP-GRAPPA embodiment of the present disclosure shows smaller NMSEs under high SNR, compared with GRAPPA.

Other parameters remain the same as used in FIG. 6. It is seen that when the SNR is low (e.g. below 30 dB), the proposed random projection method results in poorer NMSE. As SNR increases, random projection is able to improve the NMSE. This is because at high SNR, the noise reduction from Rb overweighs the system error caused by RA in Eq. [5]. When the SNR is low, the calibration matrix A is affected by larger noise and thereby the system error due to RA becomes dominant. Nevertheless, the NMSE difference is so small that GRAPPA and RP-GRAPPA can be regarded to have the same reconstruction quality.

Embodiments of the present invention can be applied to GRAPPA and other auto-calibrated reconstruction methods. When calibration is time consuming, the benefit is prominent. For example, robust GRAPPA is known to be robust to outliers but takes long in calibration. When embodiments of the present disclosure are applied to robust GRAPPA, there is a substantial savings in time. Table 1 compares both NMSEs and CPU times of robust GRAPPA with and without random projections using the first dataset.

TABLE 1

Comparison of robust GRAPPA with and without random projection (ACS = 36, ORF = 3, block = 4, column = 11, $\lambda$ = 2). The proposed random projection method shows significant CPU time savings for robust GRAPPA.

|  | Robust GRAPPA | Robust GRAPPA w/ RP |
|---|---|---|
| NMSE | 0.1036 | 0.1013 |
| CPU time (s) | 1997.7 | 41.0 |

It is seen that the NMSE of robust GRAPPA with random projection is nearly the same as that without random projection, but the former significantly saves the computation time (about 50 times).

The above experimental results demonstrate that random projection can reduce the execution time by a factor up to 5.5 for 2-D GRAPPA and 17 for 3-D GRAPPA without compromising the reconstruction quality, and when combined with PCA channel reduction, a factor up to 28. Equivalently, when the computation time is the same, random projection is able to improve the GRAPPA reconstruction quality by taking advantage of more ACS data.

EXAMPLE 2

In another embodiment of the present disclosure, each element of R is an independent random variable from the following distribution:

$$R_{(i,j)} = \sqrt{3} \begin{cases} 1 & p = 1/6 \\ 0 & p = 2/3 \\ -1 & p = 1/6 \end{cases}$$

With such a sparse binary projection matrix, a subset of equations are linearly combined in a random fashion to form a new set of equations, creating a high probability the important information is maintained in the lower dimensional space after the projection.

Since the sparse matrix has only 0s and ±1s, the computational expense of random projection can be neglected because only additions are needed. By assuming k to be 2n, and using the common GRAPPA parameters, then the size of the equation was reduced from 8,192×416 in Eq. [3] to 832×416 in Eq. [5]. The calibration process has a saving of approximately 10 times. Now the ratio between the computation time of the calibration and synthesis processes becomes 2.3. The computational expense ratio between GRAPPA and the randomly-projected GRAPPA (RP-GRAPPA) is 5.1, suggesting a saving of 5.1 times.

This embodiment was tested on a set of in vivo data downloaded from http://www.nmr.mgh.harvard.edu/~fhlin/codes/mprage_8ch_slice20.mat. The data was acquired on a 3T SIEMENS Trio system using 3-D MPRAGE sequence (TE=3.45 ms, TR=2530 ms, TI=1100 ms, Flip angle=7o, slice=20, matrix=256×256, slice thickness=1.33 mm, FOV=256 mm2) and an 8-channel head array coil. The data was acquired in full and then manually undersampled retrospectively to simulate the accelerated acquisition. Both the conventional GRAPPA and randomly-projected GRAPPA (RP-GRAPPA) were used to reconstruct the final image from reduced acquisition. All code are written in MATLAB and run on a PC with 3.4 GHz CPU and 16 GB memory, except that for FIG. 12.

For the randomly-projected GRAPPA embodiment, the random projection matrix has elements drawn from a Bernoulli distribution and reduces the dimension of the calibration equation from m to k. A factor $\lambda = k/n$ is defined, which represents how over-determined the new equation is after dimension reduction. The smaller the $\lambda$ is, the less the equation is over-determined.

To measure the accuracy of the proposed dimension reduction method, reconstructions were compared with and without dimension reduction both visually and quantitatively using normalized mean squared error (NMSE). The computational time was measured in CPU time from MATLAB.

Figure 11:
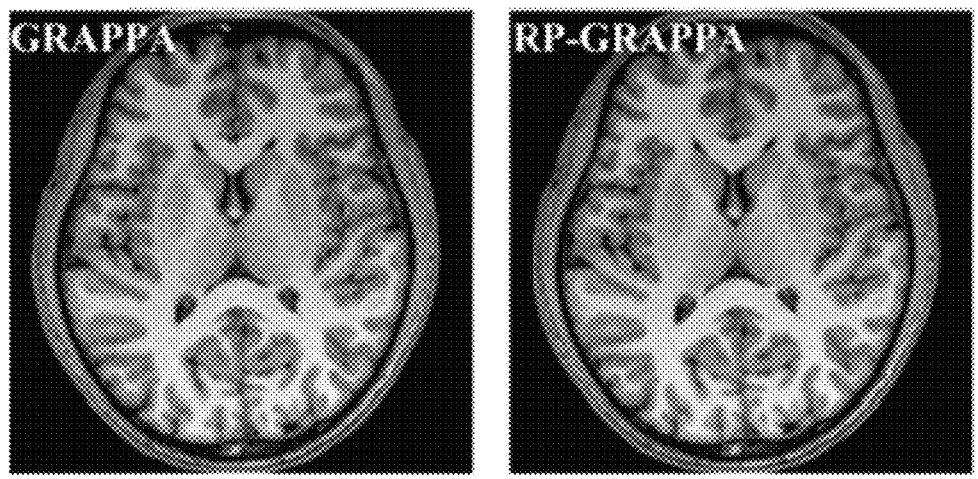
FIG. 11 is a set of images of 2D reconstructions using GRAPPA (left) and RP-GRAPPA (right)

The savings in the second example were first evaluated in 2-D reconstruction with 1-D undersampling. An ORF of 2 with 32 ACS lines was used with a net acceleration of 1.78. A single slice of the 3-D image was reconstructed. In both GRAPPA and RP-GRAPPA methods, the number of blocks $d_y$ is 4 and the number of columns $d_x$ is 13. FIG. 11 shows the reconstructions for GRAPPA (left) and RP-GRAPPA (right). The NMSEs of GRAPPA and RP-GRAPPA are 0.035 and 0.041 respectively, and the CPU times are 27.7 s and 4.6 s, respectively. The CPU time ratio between GRAPPA and RP-GRAPPA is $T_{GRAPPA}/T_{RP-GRAPPA} = 27.7/4.6 \approx 6$. Such a saving in computation time roughly agrees with our theoretical analysis. It is seen from the results that the proposed RP-GRAPPA has an NMSE about the same as the conventional GRAPPA, but saves about 6 times in the computational cost.

Figure 12:
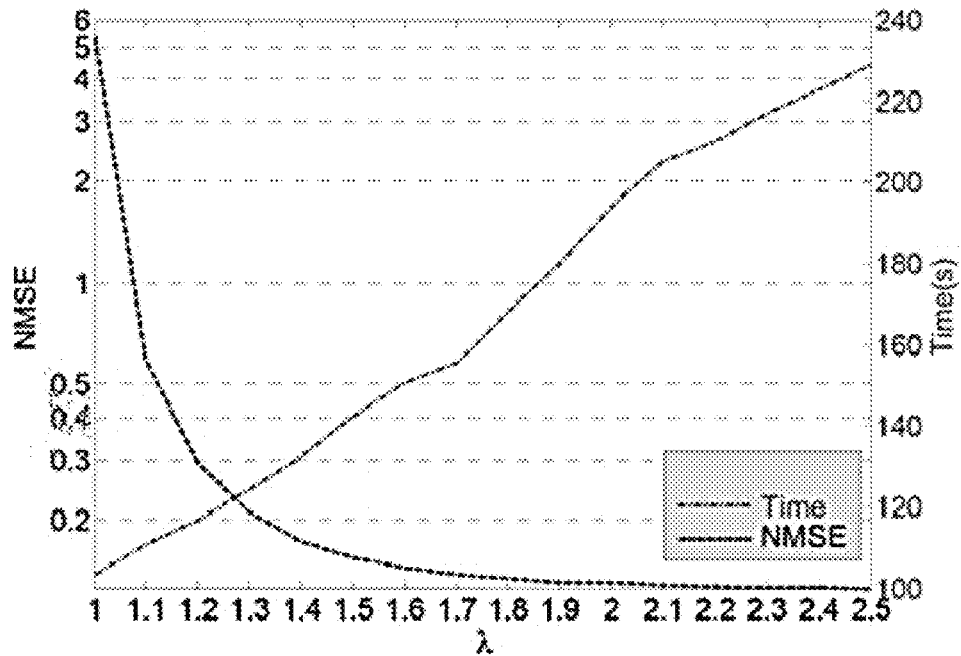
FIG. 12 is a chart showing NMSE and CPU time of the RP-GRAPPA embodiment versus λ.

In order to show the relationship between $\lambda$ and the computation time, FIG. 12 shows the curves of NMSE and CPU time for RP-GRAPPA as $\lambda$ increases from 1 to 2.5, with a step of 0.1. It is seen that the NMSE decreases rapidly (approximately in exponential) as $\lambda$ increases and becomes sufficiently low for $\lambda > 2$, while the CPU time increases only approximately linearly with $\lambda$. It should be noted that the results shown in FIG. 12 were obtained from a PC with 1.7 GHz CPU and 512 MB memory to show the increment in time with $\lambda$ more clearly.

Figure 13:
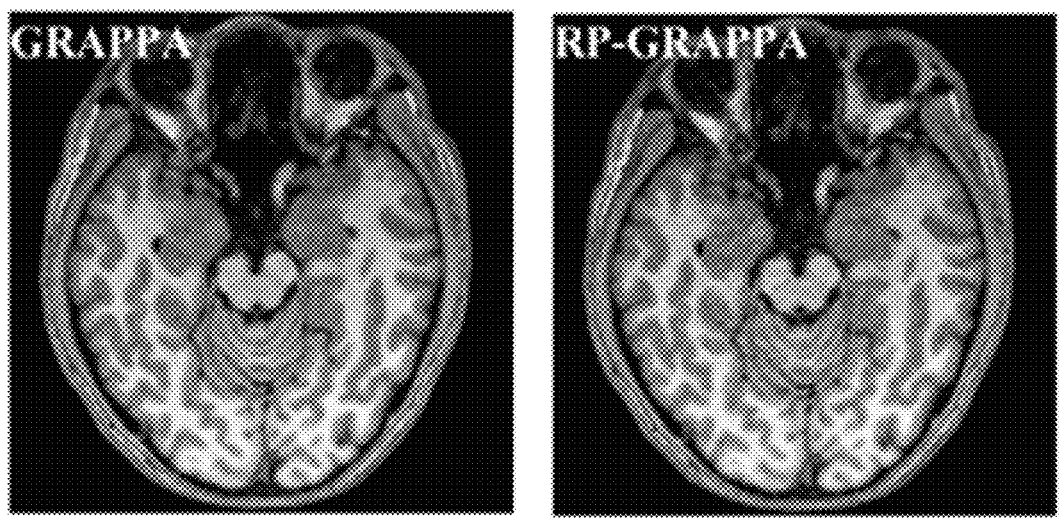
FIG. 13 is a set of images of 3D reconstruction slices using GRAPPA (left) and RP-GRAPPA (right)

Also evaluated was the performance of the proposed method in 3-D reconstructions with 1-D undersampling (only along the phase direction). An ORF of 3 with 32 ACS lines were used. In both methods, the number of blocks $d_y$ and $d_z$ are 4 and 2, respectively. The number of columns $d_x$ is 11. In FIG. 13, a single slice of the 3-D reconstructions using GRAPPA and the proposed method are compared. The NMSEs for the 3-D images are 0.38 for GRAPPA and 0.40 for RP-GRAPPA. The CPU time for GRAPPA is 16834 s, while RP-GRAPPA is 1616 s, corresponding a saving of about 10 times. Compared with GRAPPA, RP-GRAPPA saves hours in calibration time without compromising the image quality.

These experimental results demonstrate that random projection can reduce the execution time by a factor up to 6 for 2-D GRAPPA and 10 for 3-D GRAPPA without compromising the reconstruction quality. The method is expected to be especially useful for large array systems with 32 or more channels.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Although the present invention has been described with respect to one or more particular embodiments, it will be understood that other embodiments of the present invention may be made without departing from the spirit and scope of the present invention. Hence, the present invention is deemed limited only by the appended claims and the reasonable interpretation thereof.

What is claimed is:

1. A method for constructing a parallel magnetic resonance image comprising:
   receiving, at a processor, a plurality of k-space signals, each signal corresponding to a channel of a receiver coil;
   selecting, using the processor, a subset of the plurality of k-space signals, wherein the subset does not include all of the plurality of k-space signals;
   receiving, at the processor, a plurality of auto-calibration signals;
   selecting, using the processor, a subset of the plurality of auto-calibration signals;
   determining, using the processor, a first calibration equation associated with the selected auto-calibration signals and the selected k-space signals;
   reducing, using the processor, the first calibration equation to a reduced calibration equation having a lesser dimensionality than the first calibration equation;
   determining, using the processor, a plurality of reconstruction coefficients based on the reduced calibration equation, each coefficient corresponding to a channel of the receiver coil;
   synthesizing, using the processor, reconstructed k-space data based on the plurality of reconstruction coefficients and received k-space signals; and constructing, using the processor, a parallel magnetic resonance image based on the reconstructed k-space data.

2. The method of claim 1, wherein each k-space signal comprises a combination of sample data corresponding to the parallel magnetic resonance image and sensitivity information of a channel.

3. The method of claim 1, wherein the step of selecting a subset of the plurality of k-space signals is performed using principal component analysis.

4. The method of claim 1, wherein the first calibration equation is reduced by randomly selecting a subset of the first calibration equation or multiplying the first calibration equation with a random projection matrix.

5. The method of claim 4, wherein the random projection matrix comprises elements from the following distribution:

$$R_{(i,j)} = \sqrt{3} \begin{cases} 1 & p = 1/6 \\ 0 & p = 2/3 \\ -1 & p = 1/6 \end{cases}$$

6. The method of claim 1, wherein the plurality of reconstruction coefficients are determined using a least-squares method.

7. The method of claim 1, wherein the plurality of reconstruction coefficients are determined using a cost function minimization algorithm.

8. The method of claim 6, wherein the cost function minimization algorithm calculates the plurality of reconstruction coefficients under a specified constraint.

9. The method of claim 7, wherein the constraint is $l^1$-norm or $l^2$-norm.

10. The method of claim 1, wherein the plurality of reconstruction coefficients are also based on a sensitivity of the receiver coil.

11. The method of claim 1, wherein the step of selecting a subset of the plurality of k-space signals comprises:

defining, using the processor, a set of N vectors, where N equals the total number of channels associated with the plurality of k-space signals;

calculating, using the processor, a mean corresponding to each vector in the set of N vectors;

subtracting from each vector in the set of N vectors, using the processor, the calculated mean from the corresponding vector;

calculating, using the processor, a plurality of eigenvectors of a covariance matrix;

creating, using the processor, a compression matrix based on the plurality of eigenvectors; and selecting, using the processor, a subset of the plurality of k-space signals by multiplying the plurality of k-space signals by the compression matrix.

* * * * *